(12) United States Patent
Sattler et al.

(10) Patent No.: US 7,883,463 B2
(45) Date of Patent: Feb. 8, 2011

(54) COMBINATION SENSOR FOR PHYSIOLOGICAL PARAMETERS

(75) Inventors: Frank Sattler, Lübeck (DE); Jochim Koch, Ratzeburg (DE); Jörg-Uwe Meyer, Ratzeburg (DE); Michael Dowson, Northumberland (GB); Robin McWilliams, Crawslook (GB)

(73) Assignee: Dräger Safety AG & Co. KGaA, Lübeck (DE)

( * ) Notice: Subject to any disclaimer, the term of this patent is extended or adjusted under 35 U.S.C. 154(b) by 1581 days.

(21) Appl. No.: 10/952,321

(22) Filed: Sep. 28, 2004

(65) Prior Publication Data

US 2005/0101872 A1 May 12, 2005

(30) Foreign Application Priority Data

Nov. 11, 2003 (DE) ................. 103 52 626

(51) Int. Cl.
*A61B 5/00* (2006.01)
(52) U.S. Cl. .............. 600/300; 600/549; 600/500
(58) Field of Classification Search ............. None
See application file for complete search history.

(56) References Cited

U.S. PATENT DOCUMENTS

| 4,312,358 | A | * | 1/1982 | Barney | 600/483 |
| 4,883,063 | A | * | 11/1989 | Bernard et al. | 600/483 |
| 5,050,612 | A | * | 9/1991 | Matsumura | 600/483 |
| 5,673,692 | A | * | 10/1997 | Schulze et al. | 600/301 |
| 6,436,038 | B1 | * | 8/2002 | Engstrom | 600/301 |
| 6,827,487 | B2 | * | 12/2004 | Baumbach | 374/164 |
| 2003/0032893 | A1 | | 2/2003 | Koch | |
| 2004/0133081 | A1 | * | 7/2004 | Teller et al. | 600/300 |

FOREIGN PATENT DOCUMENTS

| DE | 100 38 247 A1 | 5/2001 |
| DE | 100 38 247 C2 | 5/2001 |
| DE | 101 39 705 A1 | 4/2003 |
| GB | 2 243 691 | 11/1991 |
| JP | 4-253839 | 9/1992 |
| JP | 04253839 A | 9/1992 |
| WO | WO 02/41770 A1 | 5/2002 |
| WO | WO 2004/075750 A1 | 9/2004 |

OTHER PUBLICATIONS

Machine translation of DE 10038247.*
Daniel S. Moran, 2000, Stress Evaluation by the Physiological Strain Index (PSI), *Journal of Basic and Clinical Physiology and Pharmacology*, vol. 11, Issue 4, 2000.

* cited by examiner

*Primary Examiner*—Robert L Nasser
(74) *Attorney, Agent, or Firm*—McGlew and Tuttle, P.C.

(57) ABSTRACT

A compact combination sensor is provided for physiological parameters, which can be worn behind the ear. The combination sensor has a heat flux sensor (1) for detecting two temperatures (Th1, Th2) for determining the body core temperature ($T_c$), an acoustic sensor (2) for measuring the heart rate (HR) and for detecting speech signals, as well as a measured signal evaluating unit (4, 5, 7). A communications interface (8) is provided for transmitting the processed data from the measured signal evaluating unit (4, 5, 7) to a communications unit (9) are located in the sensor carrier (11).

20 Claims, 2 Drawing Sheets

COMBINATION SENSOR FOR PHYSIOLOGICAL PARAMETERS

CROSS REFERENCE TO RELATED APPLICATIONS

This application claims the benefit of priority under 35 U.S.C. §119 of De 103 52 626.9 filed Nov. 11, 2004, the entire contents of which are incorporated herein by reference.

FIELD OF THE INVENTION

The present invention pertains to a combination sensor for physiological parameters in a sensor carrier.

BACKGROUND OF THE INVENTION

The determination and the monitoring of physiological parameters such as body temperature and heart rate (HR) is of significance for athletes and especially for firemen, who are subject to high physical stress. Various methods, specifically optical acoustic and electric methods, are known for measuring the heart rate. Various measurement methods are likewise known for determining the body temperature, DE 100 38 247 C2 specifically showing a double temperature sensor for the determination of the body core temperature ($T_c$) from the calculation-based linkage between two temperatures measured on the patient. The calculation of the body core temperature ($T_c$) from a temperature Th1 measured immediately below the skin and a near-room temperature Th2 is known from DE 101 397 05 A1.

A sensor carrier that can be worn on the body with a temperature sensor, a sensor for measuring the heart rate and a communications interface is disclosed in JP 0 425 3839 A, in: Patent Abstracts of Japan. The prior-art sensors are usually arranged on different areas of the body and operate independently from one another.

The state of stress of the person being tested can be inferred from the linkage between the body temperature ($T_c$) and the heart rate (HR) by calculating a characteristic number, for example, PSI (Physiological Strain Index), see "Stress Evaluation by the Physiological Strain Index (PSI)," Daniel S. Moran, *Journal of Basic and Clinical Physiology and Pharmacology*, Vol. 11, 4, 2000.

SUMMARY OF THE INVENTION

The object of the present invention is to provide a compact combination sensor for determining the body core temperature ($T_c$) and the heart rate (HR) and for transmitting the processed measured data.

According to the invention, a combination sensor for physiological parameters in a sensor carrier is provided with a heat flux sensor for detecting two temperatures (Th1, Th2) for the determination of the body core temperature of a user. An acoustic sensor for measuring the said heart rate and for detecting speech signals, as well as at least one measured signal evaluating unit are provided. A communications interface is provided for transmitting the processed data from the measured signal evaluating unit to a communications unit. The communications interface is also located in the sensor carrier.

An essential advantage of the combination sensor according to the invention is the compact arrangement of the sensors with the evaluating electronic unit in a single sensor carrier, which accommodates all elements and is preferably adapted to the shape of the human ear and consists of a pliable plastic material, such as silicone.

An additional, third measured signal evaluating unit may be provided for calculating a characteristic number for the physiological stress from the body core temperature ($T_c$) and the heart rate (HR) and for transmission to the communications unit.

The sensor carrier may be embedded in a pliable plastic material, preferably in silicone, and may be adapted to the shape of the human ear.

The communications unit may send signals to a receiving unit, which is equipped with a downstream display unit for displaying the heart rate (HR), the body core temperature ($T_c$) and/or the characteristic number for the physiological stress.

The sensor carrier may have a loudspeaker, which is connected with the communications interface and/or with the measured signal evaluating unit and can be activated.

The data transmission between the communications interface and the communications unit may be wireless transmission.

An exemplary embodiment of the present invention will be explained below on the basis of the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
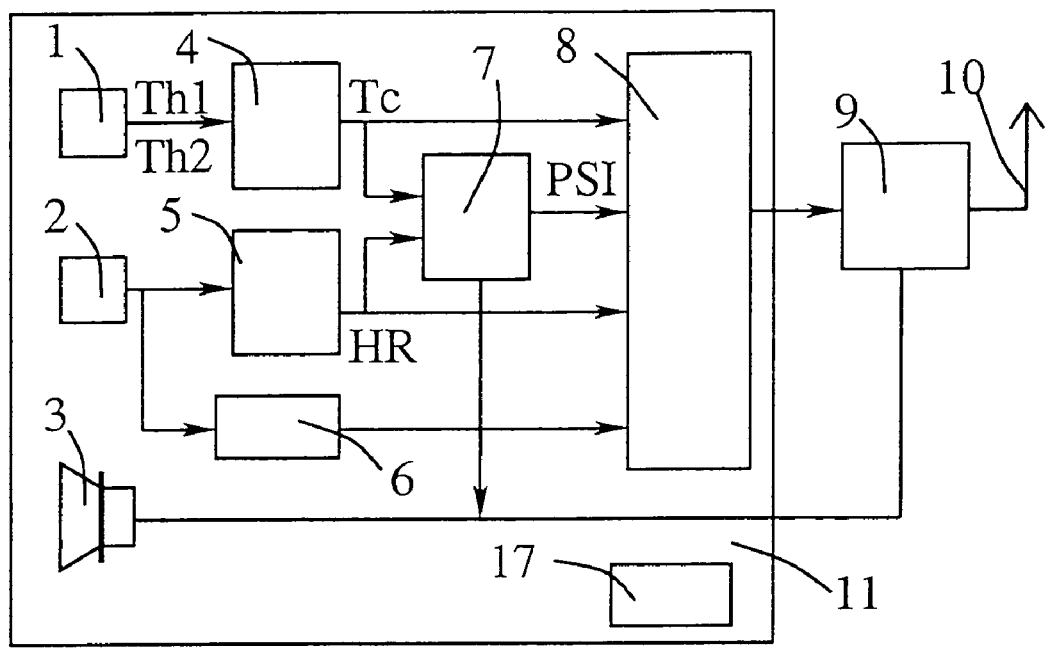
FIG. 1 is a schematic view showing the arrangement of the components of the combination sensor.

In FIG. 1, the sensor carrier 11 contains a heat flux sensor 1, which is designed especially in the form of a double temperature sensor and sends two values for the temperature (Th1, Th2), from which the body core temperature ($T_c$) is determined in the first measured signal evaluating unit 4 by means of a linkage known, for example, from DE 101 39 705 A1 (and corresponding and US Application Publication 20030032893) and DE 198 18 170 C2, the contents of each is hereby incorporated by reference in its entirety.

The acoustic sensor 2 is used to measure the heart rate (HR) and sends a time signal, which is processed in the second measured signal evaluating unit 5 to determine the heart rate (HR) in the frequency range of about 0.5 Hz to 10 Hz, wherein the time signal is at first subjected to analog or digital prefiltration in the second measured signal evaluating unit 5 and limited to the frequency range of about 0.5 Hz to 10 Hz. This is followed by the use of signal degression algorithms. The Fourier transformation and the correlation functions shall be mentioned as examples here. Analyses by means of periodograms are possible as well. In addition, the acoustic sensor 2 also records speech signals, which are separated from the overall acoustic signal at the output of the acoustic sensor 2 by means of the filter 6 in the frequency range of about 100

Hz to 3,000 Hz. This may be embodied as an analog or digital band pass filter with a band pass frequency range of about 100 Hz to 3,000 Hz.

A characteristic number for the physiological stress, especially the characteristic number PSI, is determined in the optional third measured signal evaluating unit 7 from the linkage of the values for $T_c$ and HR, and it is determined by comparison with preset, stored limit values whether an alarm shall be optionally triggered by means of the loudspeaker 3.

Figure 2:
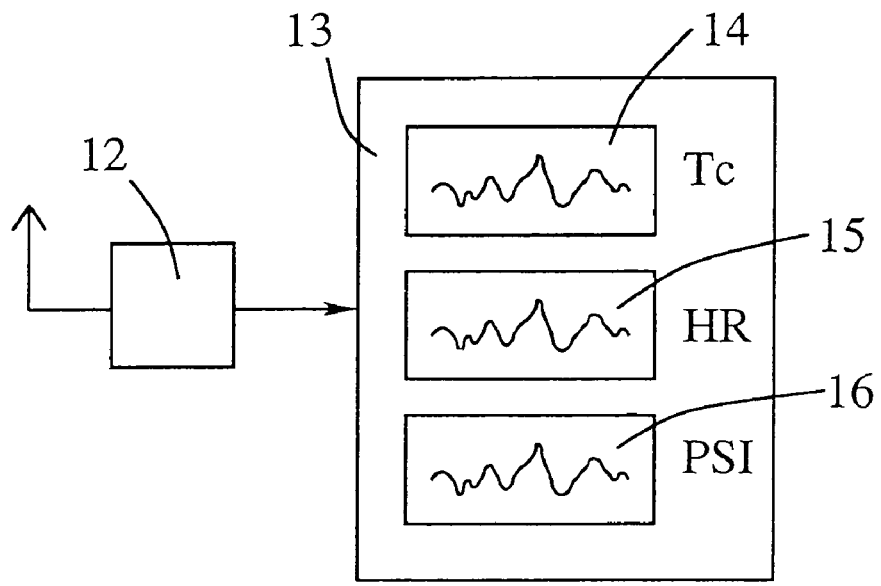
FIG. 2 is a schematic view of a receiving unit for receiving and displaying the signals received from the combination sensor.

The values $T_c$, HR and PSI as well as the speech signal from filter 6 reach the communications interface 8, in which all data are combined, compressed and digitized, i.e., processed such that they reach the communications unit 9 via a data line or preferably in a wireless manner, so that the data transmission to the receiving unit 12 takes place by means of the antenna 10 via radio, FIG. 2. The receiving unit 12 processes the signals received and separates the data $T_c$, HR and PSI, which are displayed in the downstream display unit 13 with displays 14 for HR and 16 for PSI. The components 1 through 8 are located in the sensor carrier 11 behind the ear of the person to be tested. The communications unit 9 is carried separately, for example, on the belt of the person. The communications unit 9 and the communications interface 8 may also be used to receive speech, alarm and instructions from the units 12 and 13. A speech and communications connection can also be established, for example, between firemen, who carry a combination sensor each. The power is supplied either from a battery 17 integrated in the sensor carrier 11, inductively or alternatively via the wired connection from the communications unit 9 to the communications interface 8 and thus to the sensor carrier 11. In case of, e.g., the fire department, the components 12 through 16 are located in a control center or in a mission vehicle of the head of operations. The values displayed are collected and evaluated and, as the case may be, transformed here into mission commands or alarms.

In case of an athlete, the components are located, for example, in a wristwatch in order to display the current physiological status data.

Figure 3:
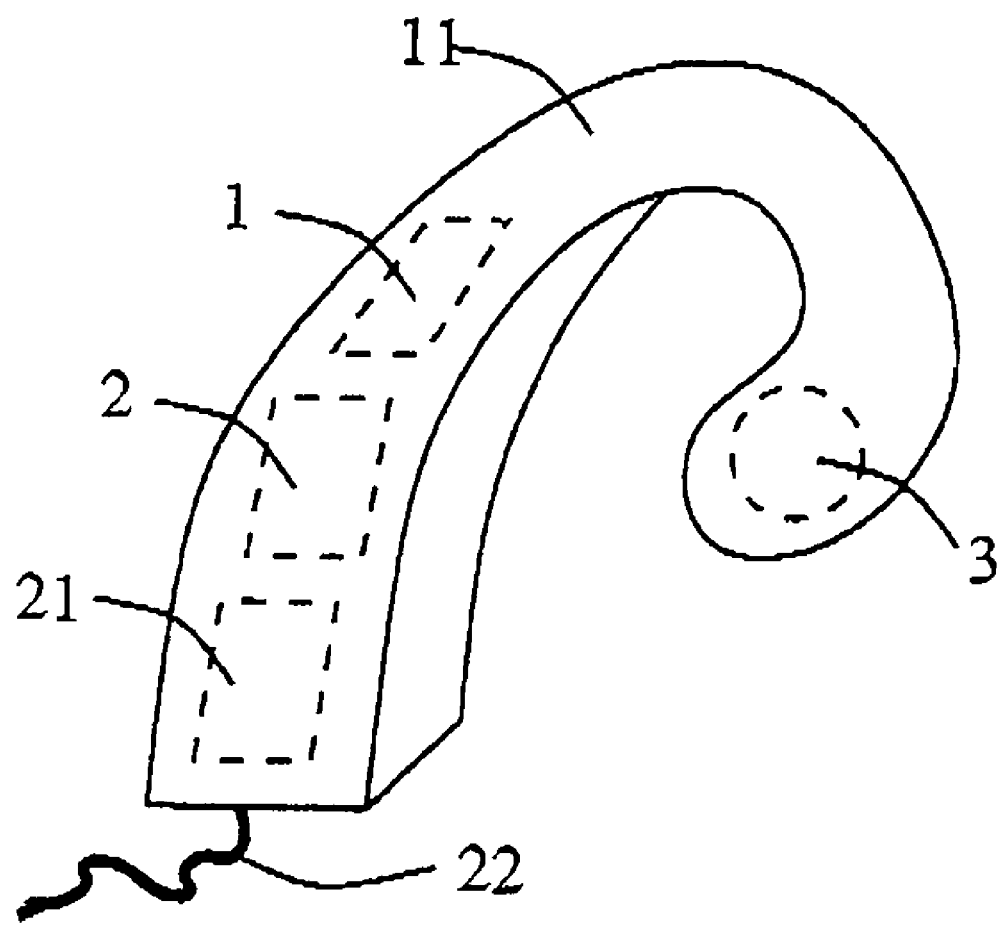
FIG. 3 is view showing the preferably one-piece design of the combination sensor, embedded in a pliable plastic material, which is adapted to the shape of the ear.

FIG. 3 shows the preferably one-piece design of the combination sensor with a sensor carrier 11 fitting the space behind the human ear with the heat flux sensor 1, the acoustic sensor 2, the loudspeaker 3, the combined electronic processing unit 21 and the data line to the communications unit 9, which line is designed as a wired connection 22 here.

The sensor carrier 11 in FIG. 3 is made, for example, of a pliable plastic material, so that adaptation of the shape to the shape and size of the individual external ear can be performed. As an alternative, the sensor carrier comprises a plurality of individual parts, which are movably connected with one another.

All sensor elements of the sensor carrier 11 touch only the skull and/or the auricle including the earlobe. This measurement position has proved to be particularly suitable for detecting good measured signals for both the temperatures for determining the body core temperature and the heart rate. There are no parts that extend into the auricular canal and can be pressed into the sensitive ear during a sudden movement. As an alternative, a combination sensor according to the present invention may also be arranged on other areas of the body that are suitable for the measurement of the body core temperature, for example, on the top of the head or in the area of the chest of the body.

While a specific embodiment of the invention has been shown and described in detail to illustrate the application of the principles of the invention, it will be understood that the invention may be embodied otherwise without departing from such principles.

What is claimed is:

1. A combination sensor for physiological parameters, the combination sensor comprising:
   a communications unit;
   a sensor carrier;
   a heat flux sensor for detecting a first temperature and a second temperature, said first temperature being the temperature at or below the skin of a person and said second temperature being the temperature of the environment;
   an acoustic sensor for measuring the heart rate and for detecting speech signals;
   a first measured signal evaluating unit and a second measured signal evaluating unit, said first measured signal evaluating unit determining a body core temperature using said first detected temperature and said second detected temperature; and
   a communications interface for transmitting the processed data from said first measured signal evaluating unit to said communications unit, said heat flux sensor, said acoustic sensor, said first measured signal evaluating unit and said second measured signal evaluating unit and said communications interface being each located at closely spaced locations in said sensor carrier to form a compact arrangement of compact sensors, wherein said sensor carrier is embedded in a pliable plastic material and is adapted to the shape of the human ear.

2. A combination sensor in accordance with claim 1, wherein an additional measured signal evaluating unit is provided for calculating a characteristic number for the physiological stress from the body core temperature and the heart rate and for transmission to the communications unit.

3. A combination sensor in accordance with claim 1, wherein said communications unit sends signals to a receiving unit, which is equipped with a downstream display unit for displaying the heart rate, the body core temperature and/or a characteristic number for the physiological stress.

4. A combination sensor in accordance with claim 1, wherein said sensor carrier has a loudspeaker or alarm which is connected with the communications interface and/or with the measured signal evaluating unit and can be activated when said processed data deviates from a preset limit value.

5. A combination sensor in accordance with claim 1, wherein said data transmission between the communications interface and the communications unit is wireless transmission.

6. A combination sensor in accordance with claim 1, wherein said heat flux sensor is shaped for being in contact with skin of the person.

7. A combination sensor for physiological parameters, the combination sensor comprising:
   a communications unit;
   a sensor carrier;
   a temperature sensor for detecting two temperatures at or near the user and for the determination of a body core temperature;
   an acoustic sensor for measuring the heart rate of the user and for detecting speech signals of the user;
   a measured signal evaluating means for receiving signals from said temperature sensor and said acoustic sensor and providing one or more processed data signals;
   a loudspeaker connected with the communications interface and/or with the measured signal evaluating means, said measured signal evaluating means comparing said signals with a preset value, said measured signal evaluating means activating said loudspeaker when the processed data is above or below said preset value; and a communications interface for transmitting the processed data from said measured signal evaluating means to said communications unit, said heat flux sensor, said acoustic sensor, said measured signal evaluating means, said filter and said communications interface being each located in said sensor carrier, wherein said sensor carrier is embedded in a pliable plastic material of silicone, and is adapted to the shape of the human ear.

8. A combination sensor in accordance with claim 7, wherein said measured signal evaluating means provides a processed data signal based on a signal received from said temperature sensor, provides a processed data signal based on a signal received from said acoustic sensor and calculates a characteristic number relating to physiological stress based on the body core temperature and the heart rate to provide a physiological stress processed data signal, wherein each of said processed data signal based on a signal received from said temperature sensor, said processed data signal based on a signal received from said acoustic sensor and said physiological stress processed data signal being transmitted to said communications unit.

9. A combination sensor in accordance with claim 7, further comprising a downstream display unit, wherein said communications unit sends signals to a receiving unit, which is equipped with said downstream display unit for displaying the heart rate, the body core temperature and/or the characteristic number for the physiological stress.

10. A combination sensor in accordance with claim 7, wherein said data transmission between the communications interface and the communications unit is wireless transmission.

11. A combination sensor in accordance with claim 7, wherein said measured signal evaluating means provides a processed data signal based on a signal received from said temperature sensor, provides a processed data signal based on a signal received from said acoustic sensor and calculates a characteristic number relating to physiological stress based on the body core temperature and the heart rate to provide a physiological stress processed data signal, wherein each of said processed data signal based on a signal received from said temperature sensor, said processed data signal based on a signal received from said acoustic sensor and said physiological stress processed data signal being transmitted to said communications unit.

12. A combination sensor for physiological parameters, the combination sensor comprising:
    a communications unit;
    a sensor carrier;
    a heat flux sensor for detecting two temperatures for the determination of a body core temperature;
    an acoustic sensor for measuring the heart rate and for detecting speech signals, said heat flux sensor and said acoustic sensor having a skin engaging portion in contact with skin of a patient;
    a measured signal evaluating unit; and
    a communications interface for transmitting the processed data from said measured signal evaluating unit to said communications unit, said heat flux sensor, said acoustic sensor, said measured signal evaluating unit and said communications interface being each closely arranged at spaced locations in said sensor carrier to form a compact arrangement of compact sensors, wherein said skin engaging portions has means for contacting the skin of a patient in an area adjacent to an ear of the patient.

13. A combination sensor in accordance with claim 12, wherein said sensor carrier is embedded in a pliable plastic material of silicone, and is adapted to the shape of the human ear.

14. A combination sensor in accordance with claim 12, further comprising a downstream display unit, wherein said communications unit sends signals to a receiving unit, which is equipped with said downstream display unit for displaying the heart rate, the body core temperature and/or the characteristic number for the physiological stress.

15. A combination sensor in accordance with claim 12, wherein said sensor carrier has a loudspeaker which is connected with the communications interface and/or with the measured signal evaluating unit and can be activated.

16. A combination sensor in accordance with claim 12, wherein said sensor carrier is shaped for being located in a space defined between an earlobe and skull of a patient.

17. A combination sensor for physiological parameters, the combination sensor comprising:
    a communications unit;
    a sensor carrier;
    a heat flux sensor for detecting a first temperature and a second temperature, said first temperature being the temperature at or below the skin of a person and said second temperature being the temperature of the environment;
    an acoustic sensor for measuring the heart rate and for detecting speech signals;
    a first measured signal evaluating unit and a second measured signal evaluating unit, said first measured signal evaluating unit determining a body core temperature using said first detected temperature and said second detected temperature; and
    a communications interface for transmitting the processed data from said first measured signal evaluating unit to said communications unit, said heat flux sensor, said acoustic sensor, said first measured signal evaluating unit and said second measured signal evaluating unit and said communications interface being each located at closely spaced locations in said sensor carrier to form a compact arrangement of compact sensors, wherein said sensor carrier is embedded in a pliable plastic material and is adapted to the shape of the human ear, said pliable plastic material being silicone.

18. A combination sensor for physiological parameters, the combination sensor comprising:
    a communications unit;
    a sensor carrier;
    a heat flux sensor for detecting two temperatures for the determination of a body core temperature;
    an acoustic sensor for measuring the heart rate and for detecting speech signals, said heat flux sensor and said acoustic sensor having a skin engaging portion in contact with skin of a patient;
    a measured signal evaluating unit; and
    a communications interface for transmitting the processed data from said measured signal evaluating unit to said communications unit, said heat flux sensor, said acoustic sensor, said measured signal evaluating unit and said communications interface being each closely arranged at spaced locations in said sensor carrier to form a compact arrangement of compact sensors, wherein said skin engaging portions has means for contacting the skin of a patient in an area adjacent to an ear of the patient, said sensor carrier having a shape such that said sensor carrier conforms to a contour the skin of the patient in an area adjacent to an ear of a patient.

19. A combination sensor for physiological parameters, the combination sensor comprising:
- a communications unit;
- a sensor carrier;
- a heat flux sensor for detecting two temperatures for the determination of a body core temperature;
- an acoustic sensor for measuring the heart rate and for detecting speech signals, said heat flux sensor and said acoustic sensor having a skin engaging portion in contact with skin of a patient;
- a measured signal evaluating unit; and
- a communications interface for transmitting the processed data from said measured signal evaluating unit to said communications unit, said heat flux sensor, said acoustic sensor, said measured signal evaluating unit and said communications interface being each closely arranged at spaced locations in said sensor carrier to form a compact arrangement of compact sensors, wherein said sensor carrier is embedded in a pliable plastic material of silicone, and is adapted to the shape of the human ear.

20. A combination sensor for physiological parameters, the combination sensor comprising:
- a communications unit;
- a sensor carrier;
- a heat flux sensor for detecting two temperatures for the determination of a body core temperature;
- an acoustic sensor for measuring the heart rate and for detecting speech signals, said heat flux sensor and said acoustic sensor having a skin engaging portion in contact with skin of a patient;
- a measured signal evaluating unit; and
- a communications interface for transmitting the processed data from said measured signal evaluating unit to said communications unit, said heat flux sensor, said acoustic sensor, said measured signal evaluating unit and said communications interface being each closely arranged at spaced locations in said sensor carrier to form a compact arrangement of compact sensors, said sensor carrier being shaped for being located in a space defined between an earlobe and skull of a patient.

* * * * *